United States Patent [19]

Bowne et al.

[11] Patent Number: 4,992,361
[45] Date of Patent: Feb. 12, 1991

[54] PHOTOGRAPHIC SILVER HALIDE MATERIALS AND PROCESS COMPRISING A PYRAZOLOTRIAZOLE COUPLER

[75] Inventors: Arlyce T. Bowne, Rochester; Sharon E. Normandin, Macedon, both of N.Y.

[73] Assignee: Eastman Kodak Company, Rochester, N.Y.

[21] Appl. No.: 365,289

[22] Filed: Jun. 12, 1989

Related U.S. Application Data

[63] Continuation of Ser. No. 23,520, Mar. 9, 1987, abandoned.

[51] Int. Cl.$^5$ ............................................. G03C 7/38
[52] U.S. Cl. .................................... 430/558; 430/386; 430/387
[58] Field of Search .................... 430/558, 386, 387

[56] References Cited

U.S. PATENT DOCUMENTS

| | | | |
|---|---|---|---|
| 4,443,536 | 4/1984 | Lestina | 430/552 |
| 4,548,899 | 10/1985 | Nakayama et al. | 430/558 |
| 4,607,002 | 8/1986 | Nakayama et al. | 430/558 |
| 4,623,617 | 11/1986 | Kaneko | 430/551 |
| 4,639,413 | 1/1987 | Kawagishi et al. | 430/387 |

FOREIGN PATENT DOCUMENTS

| | | |
|---|---|---|
| 0182617 | 11/1985 | European Pat. Off. |
| 61-120150 | 6/1986 | Japan |
| 1247493 | 9/1971 | United Kingdom |
| 1252418 | 11/1971 | United Kingdom |
| 1398979 | 6/1975 | United Kingdom |
| 1458528 | 12/1976 | United Kingdom |
| 2132783 | 7/1984 | United Kingdom |

OTHER PUBLICATIONS

Research Disclosure No. 12443, Research Discourse, vol. 124, 1974, Kenneth Mason Publications Ltd., Hampshire, England.
Research Disclosure No. 17643, Research Disclosure, vol. 176, 1978, Kenneth Mason Publications Ltd., Hampshire, England.

*Primary Examiner*—Paul R. Michl
*Assistant Examiner*—Mark R. Buscher
*Attorney, Agent, or Firm*—Richard E. Knapp

[57] ABSTRACT

Novel 1H-pyrazolo[3,2-c]-s-triazole dye-forming couplers containing in the 3-position a tertiary carbon group enable more extensive development of silver halide images in photographic silver halide materials and enable preparation of improved dispersions in photographic silver halide materials because of reduced tendency to form crystals. These couplers are useful in photographic silver halide materials and processes.

4 Claims, No Drawings

PHOTOGRAPHIC SILVER HALIDE MATERIALS AND PROCESS COMPRISING A PYRAZOLOTRIAZOLE COUPLER

This is a continuation of application Ser. No. 23,520, filed Mar. 9, 1987, now abandoned.

This invention relates to novel 1H-pyrazolo[3,2-c]-s-triazole dye-forming couplers and to photographic silver halide elements and processes using such couplers. Color images are customarily obtained in the photographic art by reaction between the oxidation product of a silver halide color developing agent and a dye-forming coupler. Pyrazolone couplers are useful for forming magenta dye images; however, pyrazolotriazole couplers represent another class of couplers that are useful for this purpose. Examples of pyrazolotriazole couplers, particularly 1H-pyrazolo[3,2-c]-s-triazoles, are described in, for instance, U.S. Pat. 4,443,536; U.K. Patents Nos. 1,247,493; 1,252,418 and 1,398,979. An example of such a 1H-pyrazolo[3,2-c]-s-triazole coupler is represented by the formula:

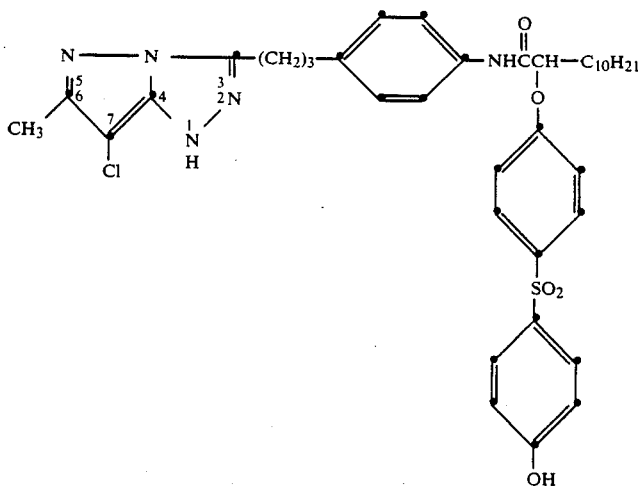

While such magenta dye-forming couplers are useful in photographic silver halide materials and processes, many of such couplers tend to crystallize in photographic silver halide elements to provide dispersions that do not provide optimum dye images. Also, strong interactions between the pyrazolotriazole nucleus and silver halide have resulted in an undesired degree of inhibition of silver development upon processing of photographic materials containing pyrazolotriazole couplers. It has been desirable to provide a pyrazolotriazole coupler which enables improved dispersions and reduced inhibition of silver halide development without sacrificing desired properties of the pyrazolotriazole couplers, such as desired maximum dye image density, narrow absorption within the desired spectral range (i.e. narrow half-bandwidth (HBW) of absorption) and without adverse effects on sensitivity.

It has been found that novel 1H-pyrazolo[3,2-c]-s-triazole dye-forming couplers containing in the 3-position a tertiary carbon group enable preparation of improved dispersions in photographic silver halide materials and reduced inhibition of silver halide development upon processing such materials.

1H-Pyrazolo[3,2-c]-s-triazole couplers, according to the invention, contain in the 3-position a tertiary carbon group

wherein:

$R_1$, $R_2$ and $R_3$ are individually halogen, such as chlorine, bromine and fluorine; alkyl, such as alkyl containing 1 to 20 carbon atoms, for example, methyl, ethyl, propyl, butyl, pentyl, ethylhexyl and eicosyl; cycloalkyl, such as cyclohexyl and cyclopentyl; amino, such as dioctylamino, dimethylamino and dodecylamino; aryl such as aryl containing 6 to 20 carbon atoms, for example, phenyl, naphthyl and mesityl; cyano; nitro; a heterocyclic group, such as a heterocyclic group comprised of atoms selected from carbon, oxygen, nitrogen and sulfur atoms necessary to complete a 5- or 6-member ring, for example, pyrrolyl, oxazolyl and pyridyl; or L-$R_5$ wherein L is a linking group that does not adversely affect the desired properties of the coupler such as, O, S, CO, CO$_2$, SO$_2$, SO

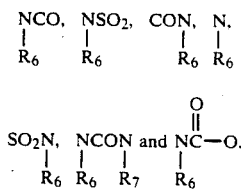

$R_6$ and $R_7$ are individually hydrogen, alkyl, such as alkyl containing 1 to 30 carbon atoms, for example, methyl, ethyl, propyl, butyl or eicosyl, or aryl, such as aryl containing 6 to 20 carbon atoms, for example, phenyl or naphthyl; or a heterocyclic group comprised of atoms selected from carbon, nitrogen, oxygen and sulfur atoms necessary to complete a 5- or 6-member heterocyclic ring, for example, pyrrolyl, oxazolyl and pyridyl. $R_5$ is a substituent that does not adversely affect the desired properties of the coupler such as alkyl containing 1 to 30 carbon atoms, for example, methyl, ethyl, propyl, butyl, pentyl and eicosyl; aryl, such as aryl containing 6 to 20 carbon atoms, for example, phenyl and napthyl; or a heterocyclic group, such as a 5- or 6-member heterocyclic group comprised of atoms selected from carbon, nitrogen, oxygen and sulfur atoms necessary to complete a 5- or 6-member heterocyclic ring, such a an oxazole, pyridine, pyrrole or thiophene ring. Optionally, in such a tertiary group, $R_1$ can form with one of $R_2$ and $R_3$ a heterocyclic ring, such as a heterocyclic ring comprised of atoms selected from carbon, nitrogen, oxygen and sulfur atoms necessary to complete a 5- or 6-member heterocyclic ring, for example, oxazole, pyridine, pyrrole and thiophene; or, $R_1$ can form with at least one of $R_2$ and $R_3$ an alicyclic ring system, such as cyclohexyl, norbornyl or adamantyl.

The groups $R_1$, $R_2$, $R_3$, $R_5$, $R_6$ and $R_7$ are unsubstituted or optionally substituted with groups that do not adversely affect the desired properties of the pyrazolotriazole coupler. The groups can be optionally substituted with, for example, halogen, such as chlorine, bromine, and fluorine; hydroxy; carboxy; cyano; nitro; alkoxy; sulfonamido; sulfamyl; amino; carbonamido; sulfonyl; aryloxy; ureido; alkyl, such as alkyl containing 1 to 20 carbon atoms, for example, methyl, ethyl, propyl and butyl; aryl, such as phenyl and naphthyl; or phenolic, carboxylic ester and heterocyclic substituent groups. Substituents can include ballast groups and coupler moieties which are known to be useful in the photographic art. Examples of useful tertiary carbon groups are

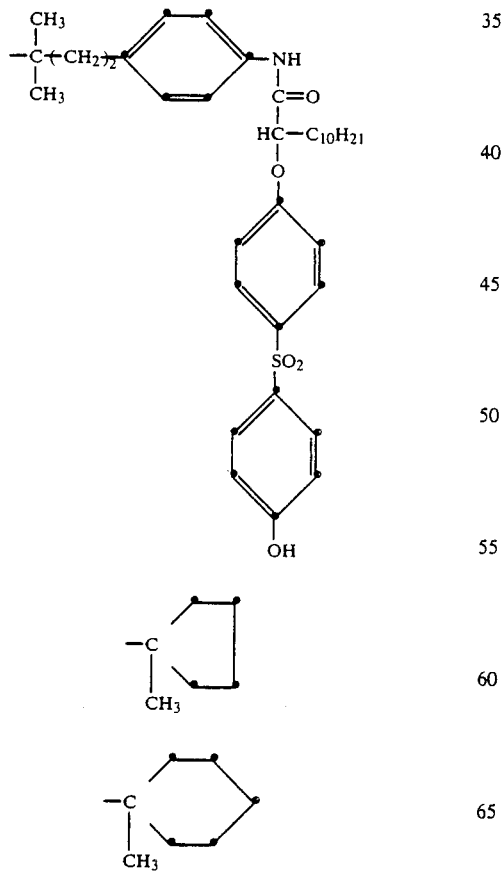

-continued

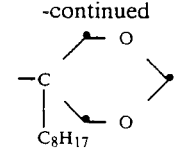
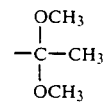
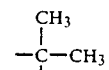
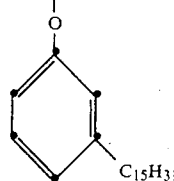
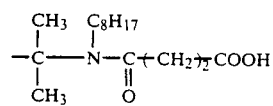
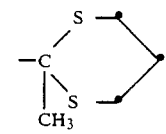
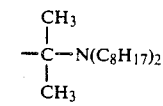
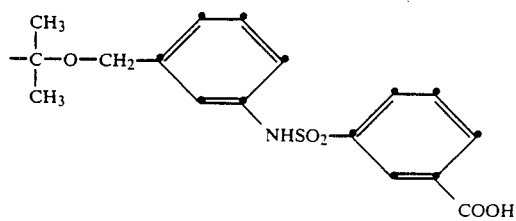
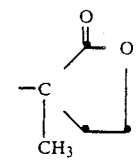
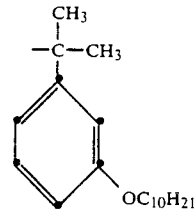
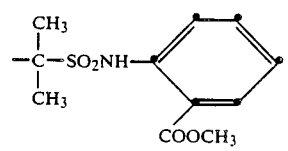

-continued
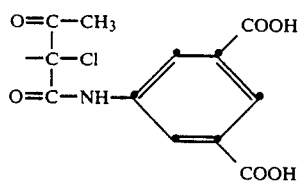
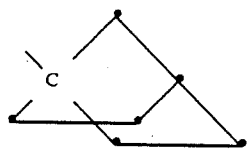
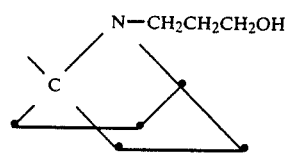
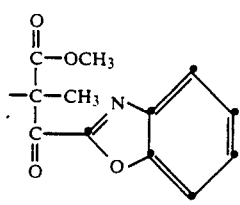
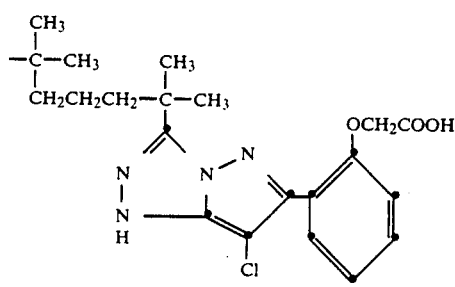
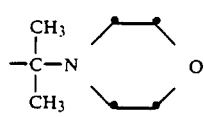
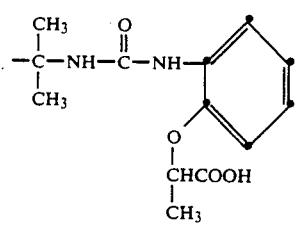
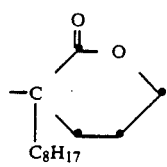
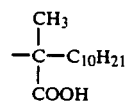
-continued
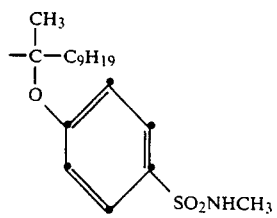
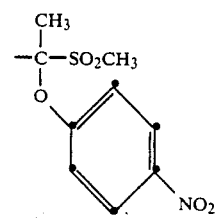
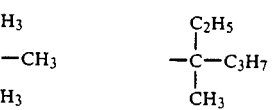
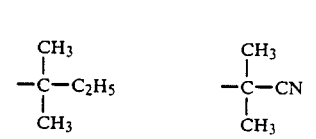
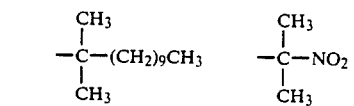
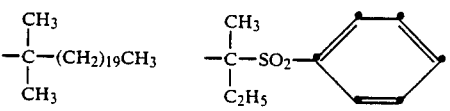
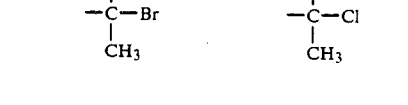
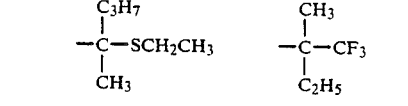
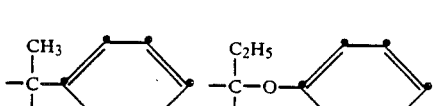
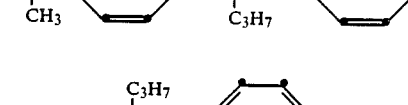
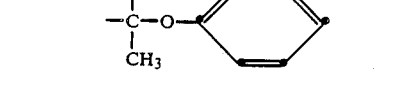

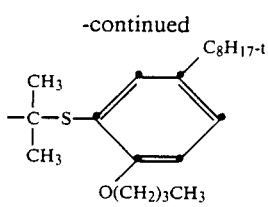

The pyrazolotriazole coupler contains in the 6-position a group $R_4$ herein which typically aids solubility. Additionally, this group can improve diffusion resistance and hue of the dye formed upon reaction of the coupler with an oxidized color developing agent. The $R_4$ group is typically an amino; such as anilino; acylamino, such as acylamino containing 2 to 20 carbon atoms, for example, acetamido, benzamido and stearamido; ureido; carboxy; alkanesulfonyl, such as ethanesulfonyl and butanesulfonyl; cyano (—CN); carbamyl, such as methyl carbamyl and hexyl carbamyl; sulfamyl, such as dioctyl sulfamyl and methyloctadecyl sulfamyl; sulfonamido, such as octanesulfonamido and benzenesulfonamido; halogen, such as chlorine, bromine or fluorine; alkyl, such as alkyl containing 1 to 20 carbon atoms, for example, methyl, ethyl, i-propyl, n-butyl and t-butyl; cycloalkyl, such as cyclohexyl and cyclopentyl; alkoxy, such as alkoxy containing 1 to 20 carbon atoms, for example, methoxy, i-butoxy and dodecyloxy; alkoxycarbonyl, such as ethoxycarbonyl and dodecyloxycarbonyl; aryloxycarbonyl, such as phenoxycarbonyl; alkylthio, such as alkylthio containing 1 to 20 carbon atoms, for example, methylthio and i-butylthio; aryl, such as aryl containing 6 to 20 carbon atoms, for example, phenyl and naphthyl; aryloxy, such as aryloxy containing 6 to 20 carbon atoms, for example, phenoxy and naphthoxy; arylthio, such as arylthio containing 6 to 20 carbon atoms, for example, phenylthio; and heterocyclic groups, such as comprised of atoms selected from the group consisting of carbon, oxygen, nitrogen and sulfur atoms necessary to complete a 5- or 6-member heterocyclic ring, such as pyridyl, benzoxazolyl, furyl and thienyl. These groups in the 6-position of the pyrazolotriazole coupler are unsubstituted or optionally substituted with groups that do not adversely affect the desired properties of the pyrazolotriazole coupler. Examples of useful substituents can include ballast groups and coupler moieties known to be useful in the photographic art; alkyl, such as alkyl containing 1 to 20 carbon atoms, for example, methyl, ethyl and t-butyl; or aryl, such as phenyl and naphthyl.

The pyrazolotriazole contains in the 7-position, that is the coupling position, hydrogen or a coupling-off group, also known as a leaving group.

Coupling-off groups, defined by Z herein, are well known to those skilled in the art. Such groups can determine the equivalency of the coupler, can modify the reactivity of the coupler, or can advantageously affect the layer in which the coupler is coated or other layers in the element by performing, after release from the coupler, such functions as development inhibition, development acceleration, bleach inhibition, bleach acceleration, color correction and the like. Representative classes of coupling-off groups include halogen, alkoxy, aryloxy, heterocycyloxy, sulfonyloxy, acyloxy, carbonamido, acyl, imido, heterocylyl, thiocyano, alkylthio, arylthio, heterocyclylthio, sulfonamido, phosphonyloxy and arylazo. They are described in, for example, U.S. Pat. Nos. 2,355,169; 3,227,551; 3,432,521; 3,476,563; 3,617,291; 3,880,661; 4,052,212 and 4,134,766; and in U.K. patents and published application Nos. 1,466,728; 1,531,927; 1,533,039; 2,006,755A and 2,017,704A; the disclosures of which are incorporated herein by reference.

Examples of specific coupling-off groups are

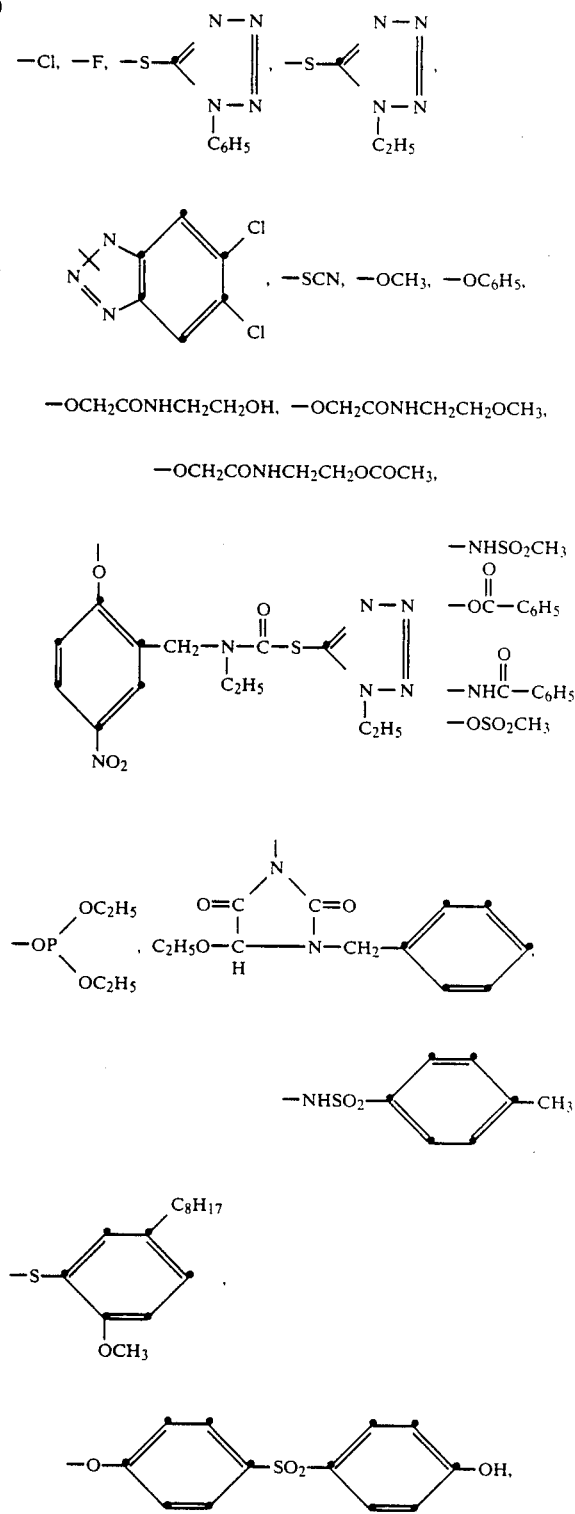

-continued

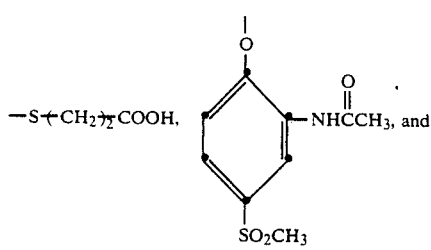

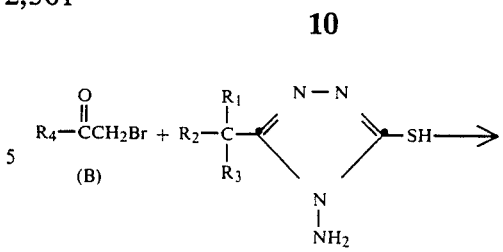

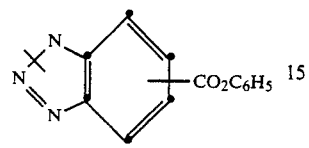

(B)

(C)

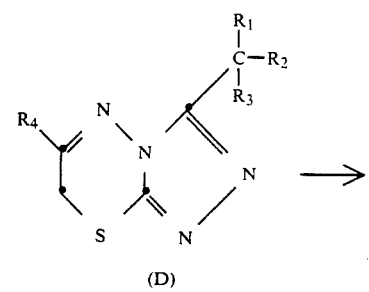

(D)

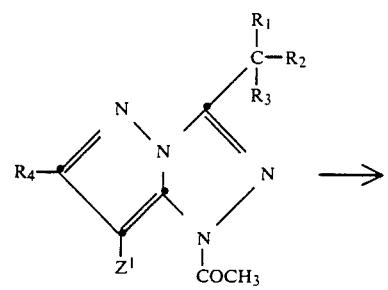

($Z^1$ is H (compound E) or —SCOCH$_3$ (compound $E^1$))

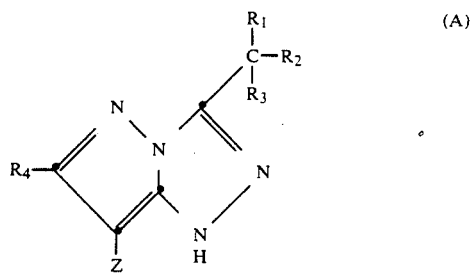

(A)

A ballast group as described is an organic radical of such size and configuration as to confer on the coupler molecule sufficient bulk to render the coupler substantially non-diffusible from the layer in which it is coated in a photographic element. Couplers of the invention may be attached to ballast groups, or to polymeric chains through one or more of the groups $R_1$ through $R_4$ or through Z as described herein. For example, one or more coupler moieties can be attached to the same ballast group. Representative ballast groups include substituted or unsubstituted alkyl or aryl groups containing 8 to 32 carbon atoms. Representative substituents include alkyl, aryl, alkoxy, aryloxy, alkylthio, arylthio, hydroxy, halogen, alkoxycarbonyl, aryloxycarbonyl, carboxy, acyl, acyloxy, amino, anilino, carbonamido, carbamoyl, alkanesulfonyl, arenesulfonyl, sulfonamido and sulfamoyl groups wherein the alkyl and aryl substituents and the alkyl and aryl portions of the alkoxy, aryloxy, alkylthio, arylthio, alkoxycarbonyl, arylcarbonyl, acyl, acyloxy, carbonamido, carbamoyl, alkanesulfonyl, arenesulfonyl, sulfonamido and sulfamoyl substitutents containing 1 to 30 carbon atoms and 6 to 30 carbon atoms, respectively, and can be further substituted with such substituents.

Illustrative 1H-pyrazolo[3,2-c]-s-triazole couplers are represented by the formula

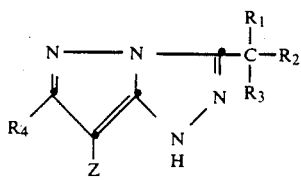

wherein $R_1$, $R_2$, $R_3$, $R_4$ and Z are as described.

Pyrazolotriazole couplers according to the invention can be used in ways and for purposes that pyrazolotriazole couplers have been used in the photographic art.

Pyrazolotriazole couplers according to the invention are prepared by the general method of synthesis described in Research Disclosure, August 1974, Item No. 12443 published by Kenneth Mason Publications, Ltd., The Old Harbourmaster's, 8 North Street, Emsworth, Hampshire P010 7DD, England. An illustrative synthetic scheme I is as follows:

wherein $R_1$, $R_2$, $R_3$, $R_4$ and Z are as described.

In this illustrative synthetic scheme I a methanol or ethanol solution of a bromoketone (B) and a triazole (C) is refluxed 1 to 20 hours to produce triazolothiadiazine (D). The product is neutralized with sodium carbonate. A thermal extrusion of sulfur from the triazolothiadiazine with concurrent ring contraction is carried out by procedures described in Research Disclosure, August 1974, Item No. 12443. However, an improvement in the sulfur extrusion from triazolothiadiazine (D) is achieved by refluxing in acetic anhydride to produce compound ($E^1$) wherein $Z^1$ is SCOCH$_3$ or by refluxing with triphenylphosphine in acetic anhydride and toluene to produce compound (E) wherein $Z^1$ is H and a small amount of compound ($E^1$). Desired pyrazolotriazole (A) wherein Z is H is obtained by treating compound (E) with potassium hydroxide (KOH) or potassium carbonate ($K_2CO_3$) or by treating compound ($E^1$) with concentrated hydrochloric acid/glacial acetic acid solution. The coupling-off group, such as chlorine, can be added by procedures known in the organic synthesis art, such as described in, for example, U.K. Patent Specification No. 1,334,515. For example, chlorine can be added as the coupling-off moiety by reaction of the pyrazolotriazole with N-chlorosuccinimide in dichloromethane. Particularly useful pyrazolotriazoles that can be prepared by this procedure are pyrazolotriazoles containing a t-butyl group in the 3-position and an aryl group, such as a substituted phenyl group, in the 6-position, with hydrogen or a coupling-off group in the coupling position (7-position).

The intermediate triazole (C) is prepared by methods known in the organic synthesis art. For example, one process is illustrated by the following reactions

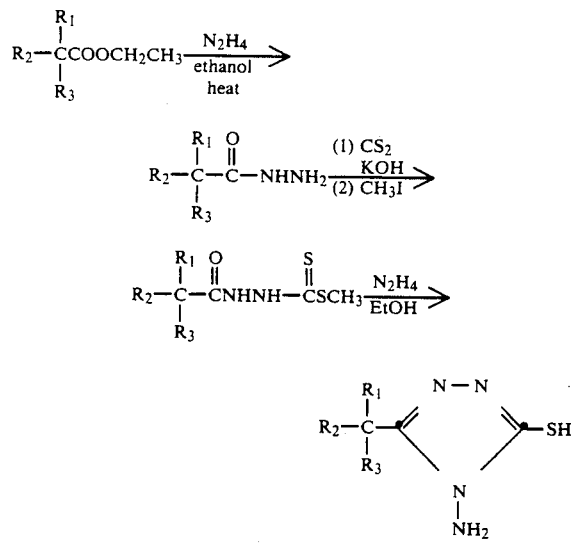

The photographic elements can be single color elements or multicolor elements. In a multicolor element, the dye-forming coupler of this invention would usually be associated with a green-sensitized emulsion, although it could be associated with an unsensitized emulsion or an emulsion sensitized to a different region of the spectrum. Multicolor elements typically contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsion sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference will be made to Research Disclosure, December 1978, Item No. 17643, the disclosures of which are incorporated herein by reference. This publication will be identified hereafter by the term "*Research Disclosure*".

The silver halide emulsions employed in the elements of this invention can be either negative-working or positive-working. Suitable emulsions and their preparation are described in *Research Disclosure* Sections I and II and the publications cited therein. Suitable vehicles for the emulsion layers of elements of this invention are described in *Research Disclosure* Section IX and the publications cited therein.

In addition to the couplers of this invention, the elements of the invention can include additional couplers as described in *Research Disclosure* Section VII, paragraphs D, E, F and G and the publications cited therein. These couplers can be incorporated in the elements and emulsion as described in *Research Disclosures* of Section VII, paragraph C and the publications cited therein.

The photographic elements of this invention or individual layers thereof, can contain, for example, brighteners (see *Research Disclosure* Section V), antifoggants and stabilizers (See *Research Disclosure* Section VI), antistain agents and image dye stabilizer (see *Research Disclosure* Section VII, paragraphs I and J), light absorbing and scattering materials (see *Research Disclosure* Section VIII), hardeners (see *Research Disclosure* Section X), plasticizers and lubricants (see *Research Disclosure* Section XII), matting agents (see *Research Disclosure* Section XVI) and development modifiers (see *Research Disclosure* Section XXI) colored masking couplers, and competing couplers.

The photographic elements can be coated on a variety of supports as described in *Research Disclosure* Section XVII and the references described therein.

Photographic elements can be exposed to actinic radiation, typically in the visible region of the spectrum, to form a latent image as described in *Research Disclosure* Section XVIII and then processed to form a visible dye image as described in *Research Disclosure* Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride,
4-amino-3-methyl-N-ethyl-N-β-(methanesulfonamido)ethylaniline sulfate hydrate,
4-amino-3-methyl-N-ethyl-N-β-hydroxyethylaniline sulfate,
4-amino-3-β-(methanesulfonamido)ethyl-N,N-diethylaniline hydrochloride and
4-amino-N-ethyl-N(-b 2-methoxyethyl)-m-toluidinedi-p-toluenesulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

EXAMPLES 1–9

The following pyrazolotriazole compounds listed in Table I were prepared. Compound C-1, C-2, C-3, C-4, C-5, C-6 and C-7 were prepared as comparison compounds.

TABLE I

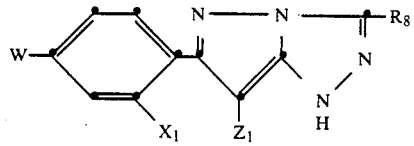

| Example No. | Cmpd. | $Z_1$ | $X_1$ | W | n | $R_8$ |
|---|---|---|---|---|---|---|
| 1 | 1 | H | H | $\underset{H(CH_2)_nCHO-}{COOH}$ | 10 | $C_4H_9\text{-}t$ |
| 2 | 2 | Cl | H | $\underset{H(CH_2)_nCHO-}{COOH}$ | 10 | $C_4H_9\text{-}t$ |
| | *(M.P. 108–110° C.) | | | | | |
| 3 | 3 | H | $CH_3$ | $\underset{H(CH_2)_nCHO-}{COOH}$ | 10 | $C_4H_9\text{-}t$ |
| | *(M.P. 78–80° C.) | | | | | |
| 4 | 4 | Cl | $CH_3$ | $\underset{H(CH_2)_nCHO-}{COOH}$ | 10 | $C_4H_9\text{-}t$ |
| | *(M.P. 72–75° C.) | | | | | |
| 5 | 5 | H | $\underset{H(CH_2)_nCHO-}{COOH}$ | H | 10 | $C_4H_9\text{-}t$ |
| 6 | 6 | Cl | $\underset{H(CH_2)_nCHO-}{COOH}$ | H | 10 | $C_4H_9\text{-}t$ |
| 7 | 7 | Cl | $\underset{H(CH_2)_nCHO-}{COOC_2H_5}$ | H | 10 | $C_4H_9\text{-}t$ |
| 8 | 8 | Cl | $CH_3$ | $\underset{H(CH_2)_nCHO-}{COOR^2}$ | 10 | $C_4H_9\text{-}t$ |
| | | | | ($R^2$ = 3:5 methyl/ethyl mixture) | | |
| 9 | 9 | | | 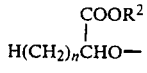 | | |
| Comparative Example A | C-1 | H | H | $\underset{H(CH_2)_nCHO-}{COOH}$ | 10 | $CH_3$ |

TABLE I-continued

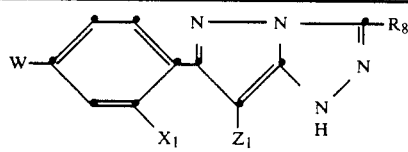

| Example No. | Cmpd. | $Z_1$ | $X_1$ | W | n | $R_8$ |
|---|---|---|---|---|---|---|
| Comparative Example B | C-2 | Cl | H | H(CH$_2$)$_n$CHO— with COOH | 10 | CH$_3$ |
| Comparative Example C | C-3 | H | CH$_3$ | H(CH$_2$)$_n$CHO— with COOH | 10 | CH$_3$ |
| Comparative Example D | C-4 | Cl | CH$_3$ | H(CH$_2$)$_n$CHO— with COOH | 10 | CH$_3$ |
| Comparative Example E | C-5 | Cl | CH$_3$ | H(CH$_2$)$_n$CHO— with COOH | 16 | CH$_3$ |
| Comparative Example F | C-6 | Cl | CH$_3$ | H(CH$_2$)$_n$CHO— with COOCH$_3$ | 10 | CH$_3$ |
| Comparative Example G | C-7 | | | (see structure below) | | |

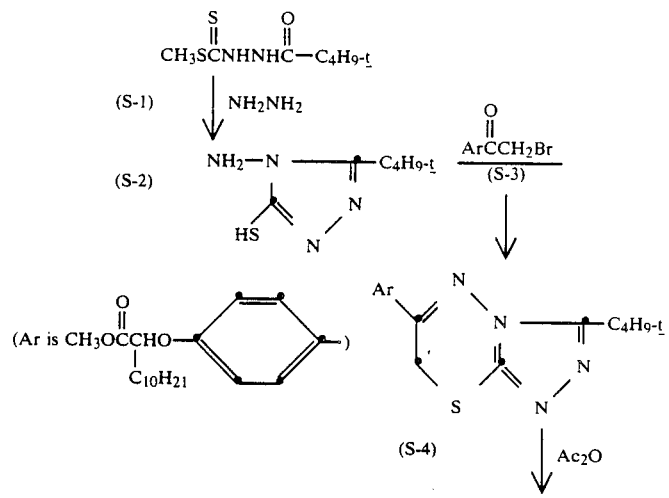

*M.P. herein means melting point.

EXAMPLE 1

Preparation of Compound 1

This preparation was carried out as follows:

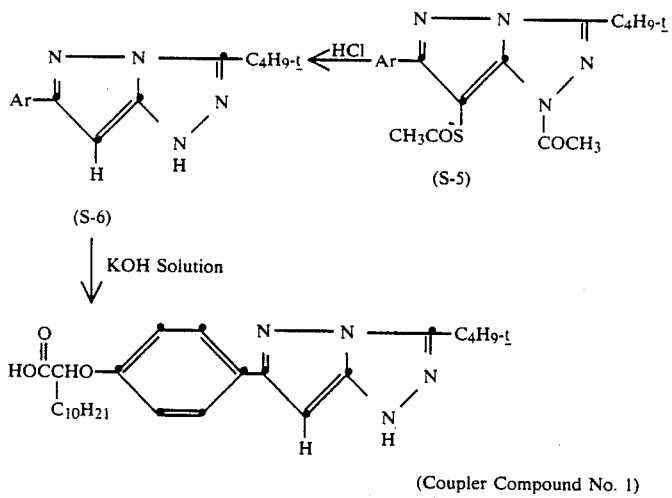

(Coupler Compound No. 1)

A solution of 2.92 gm (14.2 mmol) methyl 2-pivaloyl-dithiocarbazate (S-1) and 2.85 gm (56.8 mmol) hydrazine hydrate in 15 ml ethanol was refluxed 2 hours, cooled, concentrated, and acidified to give 1.2 gm off-white crystals with nmr and mass spectra consistent with S-2. More of this product was obtained in a repeat run. A solution of 4.8 gm (27.9 mmol) of S-2 and an equimolar amount of alpha-bromo-4-(1-carbomethoxyundecyloxy)acetophenone (S-3) in 50 ml methanol was refluxed 20 hours, concentrated, neutralized with potassium carbonate solution, and filtered to give 7.3 gm tan solid with the expected nmr spectrum for S-4. This product was then refluxed in 20 ml acetic anhydride 30 minutes, concentrated, and triturated with hexane to yield 5.3 gm off-white solid S-5. Next, refluxing a solution of S-5 in 1.5 ml concentrated hydrochloric acid and 10 ml methanol 30 minutes gave, on workup 3.9 gm orange glassy ester S-6. Finally, this was hydrolyzed by treating 20 minutes with 2.26 gm potassium hydroxide in 20 ml each of water, methanol, and tetrahydrofuran. Acidification, extraction, and isolation provided 3.0 gm white solid with nmr and mass spectra consistent with carboxylic acid Compound 1. The nmr and mass spectral analysis provided the following:

Compound 1 NMR (DMSO-$d_6$): δ (ppm) 0.85 (s, 3H); 1.1–1.4 (s, 16H); 1.45 (s, 9H); 4.6 (t, 1H); 6.0 (s, 1H); 6.9 (d, 2H); 7.85 (d, 2H). FDMS: m/e 454

EXAMPLE 2

Preparation of Compound 2

To improve product isolation the overchlorinated derivative was made, then converted to the monochloro product with ascorbic acid, A stirred solution of 2.25 gm (5 mmol) Compound 1 in 10 ml dichloromethane and 5 ml methanol was treated portionwise with 0.82 gm (6.3 mmol) N-chlorosuccinimide and a foamy solid product was isolated. This was dissolved in 10 ml methanol and treated with 0.92 gm (5.25 mmol) ascorbic acid in 9.25 ml of 1N aqueous sodium hydroxide solution. Extraction and purification gave 1.9 gm off-white solid with the nmr and mass spectra expected for Compound 2. The nmr and mass spectral analysis provided the following:

4 lb: δ (ppm) 0.85 (m, 3H); 1.1–1.4 (broad s, 16H); 1.55 (s, 9H); 1.9–2.1 (m, 2H); 4.75 (t, 1H); 7.05 (d, 2H); 7.95 (d, 2H). FDMS: m/e 488 mp 108°–110° C.

EXAMPLES 10–15

Photographic elements were prepared by coating a cellulose acetate-butyrate film support with a photosensitive layer containing a silver bromoiodide emulsion at 0.91 gm Ag/m² gelatin at 3.77 gm/m², and one of the couplers designated in Table II dispersed in half its weight of tricresyl phosphate and coated at 1.62 mmol/m². The photosensitive layer was overcoated with a layer containing gelatin at 1.08 gm/m² and bis-vinylsulfonylmethyl ether at 1.75 weight percent based on total gelatin.

Samples of each element were imagewise exposed through a graduated-density test object and processed at 40° C. employing the following color developing solution, then stopped, bleached, fixed, washed, and dried to produce stepped magenta dye images.

| | |
|---|---|
| $K_2SO_3$ | 2.0 gm |
| $K_2CO_3$ | 30.0 gm |
| KBr | 1.25 gm |
| KI | 0.6 gm |
| 4-Amino-3-methyl-N-ethyl-N-2'-hydroxyethylaniline sulfate | 3.55 gm |
| Water to 1.0 liter, pH | 10.0 |

Densitometry of these images provided measures of relative photographic speed (S), maximum density ($D_{max}$), and contrast (gamma γ) while x-ray fluorescence gave the total developed silver at maximum dye density (Ag in mg/m²). Dye hues were obtained from spectrophotometric curves by measuring the maximum absorption peak (λmax) normalized to 1.0 density, and the half-bandwidth (HBW). These data are summarized in Table II. Similar measurements of dye hue half-bandwidth (HBW') were made on low coupler coatings containing one-third the normal coupler levels and the degree of absorption broadening for typical examples is reported in Table III.

TABLE II

| Example No. | Cpd | S | $D_{max}$ | Ag | γ | $\lambda_{max}$ |
|---|---|---|---|---|---|---|
| 10 | 2 | 367 | 3.65 | 538 | 1.37 | 575* |
| 11 | 3 | 369 | 3.11 | 689 | 1.47 | 569 |
| 12 | 4 | 355 | 3.26 | 495 | 1.47 | 564 |
| 13 | 5 | 358 | 2.95 | 558 | 1.43 | 564 |

TABLE II-continued

| Example No. | Cpd | S | $D_{max}$ | Ag | γ | $\lambda_{max}$ |
|---|---|---|---|---|---|---|
| 14 | 6 | 353 | 1.99 | 517 | 1.03 | 560 |
| 15 | 9 | 358 | 2.57 | 506 | 0.87 | 557 |
| Comparative Example H | C-8 | 354 | 3.54 | 474 | 1.03 | 554 |
| Comparative Example I | C-2 | 353 | 2.91 | 495 | 1.20 | 544 |
| Comparative Example J | C-4 | 260 | 2.15 | 344 | 0.97 | 563 |
| Comparative Example K | C-7 | 335 | 2.25 | 350 | 0.80 | 560 |

*Because this coating was fogy, this value is unreliable.

Structures of comparison couplers are shown in Table I and below:

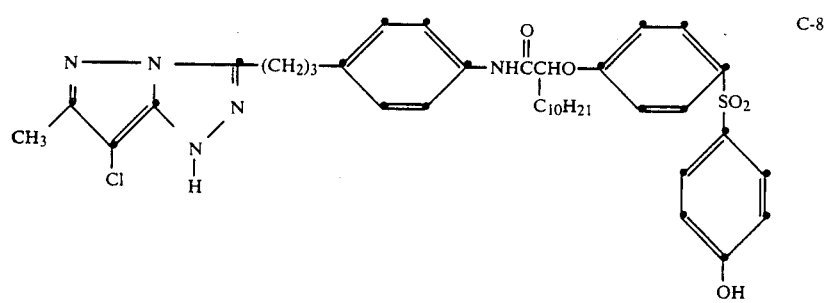

TABLE III

| | | Width in Nanometers | | |
|---|---|---|---|---|
| Example No. | Cpd | HBW | HBW' | Broadening |
| Comparative Example L | C-8 | 86 | 107 | 21 |
| Comparative Example M | C-7 | 87 | 100 | 13 |
| 16 | 9 | 79 | 88 | 9 |

It can be seen from the data in Table II that the compounds of this invention provide higher photographic speed, density, and contrast than comparison compounds in which the substituent in the 3-position is methyl rather than t-butyl. In addition, the inventive compounds allow more silver to develop than do the comparison pyrazolotriazole couplers including C-8. Table III shows that compounds of the invention, because of their bulky substituents in the 3-position, also inhibit undesired dye aggregation which can lead to undesirable hue shifts and loss of hue purity due to absorption broadening.

EXAMPLE 17

Coupler Dispersability

During the preparation of coatings for the photographic materials according to Table II, a few drops of each coupler dispersion were spread on a glass slide and examined under a microscope as the dispersion dried. Severe crystallization was noted for comparison compounds C-2 and C-4 while few, if any, crystals could be seen for inventive compounds 2 and 4. This is surprising since it might be expected that the molecular weight increase on replacing a methyl with a t-butyl group would make crystallization more likely. The couplers of the invention contain sufficient bulkiness of the substituent in the 3-position to prevent the close approach of adjacent pyrazolotriazole molecules needed for crystallization.

The invention has been described in detail with particular reference to preferred embodiments thereof, but it will be understood that variations and modifications can be effected within the spirit and scope of the invention.

What is claimed is:

1. In a photographic element comprising a support, a photographic silver halide emulsion, and a magenta dye-forming 1H-pyrazolo[3,2-c]-s-triazole coupler, the improvement wherein
the 1H-pyrazolo[3,2-c]-s-triazole coupler contains in the 3-position a tertiary carbon group

wherein $R_1$, $R_2$ and $R_3$ are individually alkyl.

2. A photographic element as in claim 1 wherein the 1H-pyrazolo[3,2-c]-s-triazole coupler contains in the 3-position a tertiary butyl group.

3. A photographic element as in claim 1 wherein the 1H-pyrazolo[3,2-c]-s-triazole coupler is

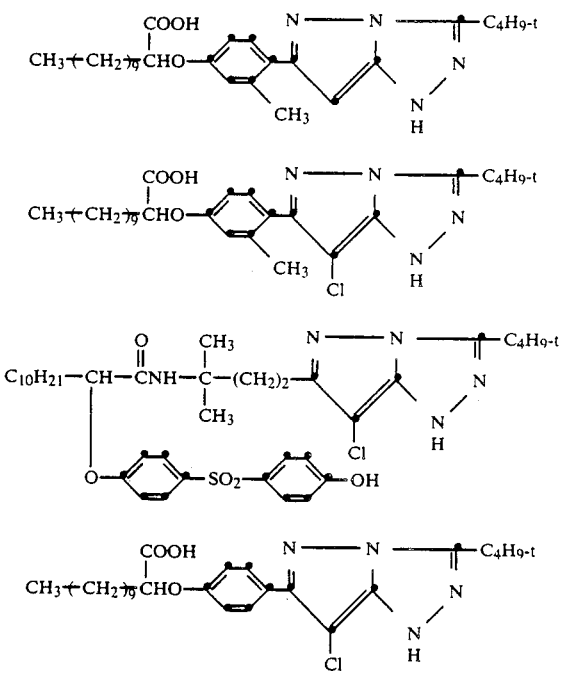

-continued
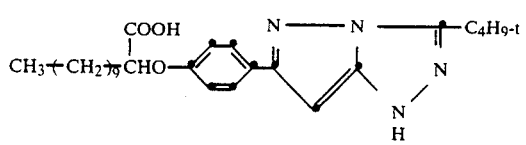
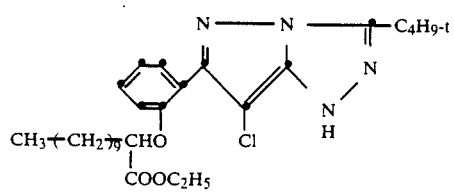
-continued or
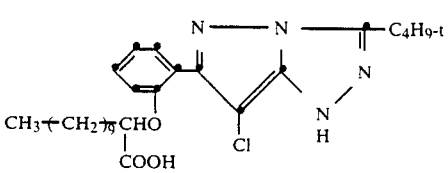
4. A process of forming a magenta dye image in an exposed photographic element as defined in claim 1, said process comprising developing the exposed photographic element with a silver halide color developing agent.
* * * * *